United States Patent [19]

Limousin et al.

[11] Patent Number: 5,318,594

[45] Date of Patent: * Jun. 7, 1994

[54] DDD TYPE CARDIAC PACEMAKER HAVING AUTOMATIC OPERATING MODE SWITCHING

[75] Inventors: Marcel Limousin; Sylvie Girodo, both of Montrouge; Odile Malherbe, Cachan, all of France

[73] Assignee: ELA Medical, Montrouge, France

[ * ] Notice: The portion of the term of this patent subsequent to has been disclaimed.

[21] Appl. No.: 813,437

[22] Filed: Dec. 24, 1991

Related U.S. Application Data

[63] Continuation-in-part of Ser. No. 622,709, Dec. 6, 1990, abandoned.

[30] Foreign Application Priority Data

Nov. 30, 1990 [FR] France .................................. 90 15013

[51] Int. Cl.⁵ .............................................. A61N 1/368
[52] U.S. Cl. .............................................................. 607/9
[58] Field of Search ............... 128/419 PG; 607/9, 14, 607/15

[56] References Cited

U.S. PATENT DOCUMENTS

| 4,802,483 | 2/1989 | Lindgren | 128/419 PG |
| 4,944,298 | 7/1991 | Sholder | 128/416 PG |
| 5,133,350 | 7/1992 | Duffin | 128/419 PG |

FOREIGN PATENT DOCUMENTS

| 0360668 | 3/1990 | Europen Pat. Off. | A61N 1/368 |
| 0238966 | 9/1987 | Europen Pat. Off. | A61N 1/368 |

OTHER PUBLICATIONS

The American Journal of Cardiology, vol. 52 No. 1, Jul. 1983, pp. 88-91; Rubin et al.; "Current physiologic pacemakers: a serious problem with a new device".

Girodo et al., "Improved Dual Chamber Pacing Mode In Paroxysmal Atrioventricular Conduction Disorders" PACE, vol. 13, Dec. 1990, Part II, pp. 2059-2064.

"Clinical Benefits of Automatic Upper Rate Behaviour in Dual Chamber Pacemakers", VITATEXT, Product Management Department, Vitatron Medical, Dieren, The Netherlands, Nr. 1, 1990, pp. 3-5.

U. Stierle et al., "A-V Delay Hysteresis: First Clinical Results", VITATEXT, Vitatron Medical Velp., The Netherlands, Nr. 1, 1990, pp. 10-14.

A. Sinnaeve et al., "Advantages of a Software Controlled Atrial Refractory Period in DDD Pacemakers", VITATEXT, Nr. 1, 1990, pp. 6-9.

Primary Examiner—William E. Kamm
Assistant Examiner—Kennedy J. Schaetzle
Attorney, Agent, or Firm—Davis Hoxie Faithfull & Hapgood

[57] ABSTRACT

A cardiac pacemaker that is programmable to have one of a DDD and an AAI pacing mode of operation such that the pacing mode best suited to the patient's physiological condition is selected and implemented. The heart is paced in the AAI mode during periods of atrio-ventricular conduction. It automatically switches to pacing the heart in the DDD mode in response to a lack of atrio-ventricular conduction, and automatically switches back to the AAI mode after occurrence of a restoration event including restoration of atrio-ventricular conduction. Time delays for use in the DDD mode are calculated during operation in the AAI mode prior to loss of atrio-ventricular conduction and other timing delays for monitoring the patient's current physiological condition for mode switching are calculated.

40 Claims, 3 Drawing Sheets

Microfiche Appendix Included
(1 Microfiche, 66 Pages)

DDD TYPE CARDIAC PACEMAKER HAVING AUTOMATIC OPERATING MODE SWITCHING

RELATED APPLICATIONS

This application is a continuation-in-part of U.S. patent application Ser. No. 622,709 entitled Cardiac Pulse Generator of the DDD Type With Automatic Operation Mode Switching, filed Dec. 6, 1990 in the names of Marcel Limousin, Sylvia Girodo and Odile Malherbe, now abandoned.

This specification is accompanied by a microfiche appendix of one sheet.

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

FIELD OF THE INVENTION

This invention relates to a cardiac pacemaker having a DDD mode of pacing operation, more particularly to automatically switching operation between the DDD mode and the AAI mode of pacing in response to physiological changes of the patient.

BACKGROUND OF THE INVENTION

Isolated sinusal dysfunctions, or those within the scope of the atrial illness, raise a question as to the choice of the optimal pacing mode. A single-chamber pacemaker for atrial pacing in the AAI operating mode appears most appropriate However, when the sinus deficiency extends to the bundle of His, paroxystic atrio-ventricular block may appear intermittently or completely. When it does appear, there is no atrio-ventricular conduction or spontaneous depolarization of the ventricle (the latter is also referred to as "ventricular detection"). In this situation, as long as the block exists, there is a need to provide pacing of the ventricle.

Therefore, as a safety measure, it has been the practice in such circumstances to implant a dual-chamber pacemaker which operates in the DDD mode to pace systematically the atrium and the ventricle. However, outside of a period of crisis, i.e., when there is no atrio-ventricular block, ventricle pacing is not necessary. A problem with ventricle pacing at such time is that it can cause competition between the paced and spontaneous depolarizations, and pacing consumes added energy for such unneeded pulses which shortens the useful life of an implanted, battery-operated pacemaker.

There is thus a continuing need for cardiac pacemakers having improved operating characteristics for pacing hearts that undergo temporary periods of crisis. There is a further need for more efficient and more adaptive pacemakers that change the pacing operating mode in response to physiological changes of the patient.

SUMMARY OF THE INVENTION

It is therefore, an object of the present invention to provide a cardiac pacemaker that is capable of pacing the ventricle only during a period of crisis. It is another object to provide a more energy efficient pacemaker.

It is another object of this invention to provide a cardiac pacemaker of the DDD type that will operate in the DDD mode solely during period of crisis, and will operate in the AAI mode outside of the period of crisis.

It is a further object of the invention is to provide a pacemaker that will automatically switch from one operation mode to the other in response to a change in the physiological condition of the patient. It is another object to provide for operating in the new mode with automatically optimized parameters not requiring reprogramming of the pacemaker.

The present invention is directed to improving a cardiac pacemaker that is programmable to have one of a DDD and an AAI pacing mode of operation such that the pacing mode best suited to the heart physiological condition is selected and implemented. Broadly, the invention is directed to methods and apparatus for providing the DDD type pacemaker with automatic switching between modes of pacing operation.

In one embodiment, the invention concerns pacing the heart in the AAI mode during atrio-ventricular conduction periods, and automatically switching to pacing the heart in the DDD mode in response to a lack of atrio-ventricular condition, and automatically switching back to the AAI mode after atrio-conduction is restored.

Preferably, switching from the AAI mode to DDD mode occurs after the occurrence of an atrial event outside of an established refractory period, which triggers a ventricular surveillance delay, such that there is no atrio-ventricular conduction during the surveillance delay. Accordingly, satisfaction of this condition results in switching automatically from the AAI to the DDD mode. This results in pacing the ventricle.

Thereafter, each time atrio-ventricular conduction is restored, the operating mode automatically switches back to the AAI mode and each time conduction is again lost, the operating mode switches to the DDD mode.

Preferably, the ventricular surveillance delay is selected to equal the average value of a selected number of intervals between one atrial event and the subsequent ventricular detection (i.e., a spontaneous ventricular depolarization) during that preceding number of cycles, plus a predetermined time. This delay provides for sufficient time to detect the occurrence of a spontaneous atrio-ventricular conduction responsive to the atrial event.

More preferably, the ventricular surveillance delay equals the average value of the intervals between one atrial event and the subsequent ventricular detection during from 4 to 16, preferably eight, preceding cycles, and the predetermined time is selected from between 16 and 78 ms, preferably 47 ms, and more preferably 31 ms. In addition, the ventricular surveillance delay may be restricted to a maximum period of about 350 ms.

At the time of switching to the DDD mode, the atrio-ventricular delay (AVD), i.e., the period of time that elapses following an atrial event at which the ventricle will be paced if no spontaneous depolarization is detected, is calculated through linear interpolation between a maximum value and a minimum value, as a function of the sinus rhythm. Preferably, the maximum and minimum values of the atrio-ventricular delay are determined during the periods of spontaneous atrio-ventricular condition preceding the loss of atrio-ventricular conduction, and are the maximum and minimum values of the time between the atrial event and the ventricular detection during that period, respectively.

More preferably, the maximum value of the atrio-ventricular delay is determined and stored, e.g., in a memory device, when the sinus (atrial) rhythm is between the programmed basic pacing rate limit (also known as the minimum pacing rate) and the basic pacing rate increased by 12.5 percent. Similarly, the minimum value of the atrio-ventricular delay is preferably determined and stored when the sinus rhythm is between the programmed upper pacing rate limit (also known as the maximum pacing rate) and the upper pacing rate less 12.5 percent thereof. The upper and basic pacing rates are typically programmed by the physician in accordance with the patient's condition when the pacemaker is implanted.

In accordance with the present invention, upon each change from an atrial detection to an atrial pacing, a calculation is made of an extension of the atrio-ventricular delay that is equal to the difference between, on the one hand, the interval between the atrial pacing and the next ventricular detection, and on the other hand, the interval between the atrial detection and the next ventricular detection. The latter interval is measured during the antepenultimate cycle to the switch.

Further, upon each change from an atrial pacing to an atrial detection, a calculation is made of an extension of the atrio-ventricular delay that is equal to the difference between, on the one hand, the interval between the atrial pacing and the next ventricular detection, and on the other hand, the interval between the atrial detection and the next ventricular detection. In this case the first interval is measured during the antepenultimate cycle to the switch.

In connection with switching from the DDD to the AAI modes, this is done on a determined restoration of atrio-ventricular conduction. Such a restoration event includes, without limitation, satisfaction of one of the following conditions:

(a) changeover from a paced atrial activity to an atrial detection,
(b) recovery of a spontaneous ventricular activity,
(c) after one hundred cycles with ventricular pacing, and
(d) when the spontaneous detection or pacing rate becomes less than a selected reference frequency.

Regarding condition (b), the switching back to the AAI mode occurs automatically if, during a selected number of consecutive cycles, e.g., sixteen, the pacemaker detects R waves that are synchronous with atrial events. Regarding condition (d), the reference frequency is selected to correspond to the basic escape interval less a selected time period, e.g., between 16 and 94, preferably 31 ms.

Upon changing from atrial detection to atrial pacing, the atrial escape interval is shortened, during at most eight cycles, by a programmed value, for increasing the rate of the atrial pacing so as to compensate the drop of the cardiac output.

BRIEF DESCRIPTION OF THE DRAWINGS

Further features of the invention, its nature and various advantages will be more apparent from the accompanying drawings and the following detailed description of the invention, in which like reference numerals and characters refer to the elements and parameters, and in which.

DETAILED DESCRIPTION OF THE INVENTION

According to the present invention, a pacemaker of the DDD type is implanted in patients having an indication of atrial pacing and with whom there may, in addition, be an indication of crisis resulting from a lack of atrio-ventricular conduction. Advantageously, the pacemaker having automatic mode switching in accordance with the present invention is operating in an "automatic DDD mode", meaning that, outside of atrio-ventricular conduction crisis periods, it operates in the AAI mode, and it automatically switches over to the DDD mode upon the appearance of trouble in the atrio-ventricular conduction, and it will automatically revert to the AAI mode when one of certain conditions is met.

When the automatic DDD mode is in use, the pacemaker of the present invention offers operation in the AAI pacing mode which allows the spontaneous atrial conduction to express itself. However, as soon as a slowdown of the conduction appears, the pacemaker switches over to the DDD mode and operates with parameters automatically optimized during the preceding AAI mode of operation, and without requiring these parameters to be reprogrammed by a physician.

The pacemaker will operate in the AAI mode as long as the atrio-ventricular conduction is normal, that is, as long as each atrial event E (outside of the refractory periods) is followed by a synchronous ventricular detection R. An atrial event E is either an atrial detection P (i.e., a spontaneous atrial depolarization) or an atrial pacing A (e.g., caused by a stimulating pacing pulse), which respectively initiate a PR or AR interval. This interval is designated in a general manner as ER.

ATRIAL DETECTION

Figure 4:
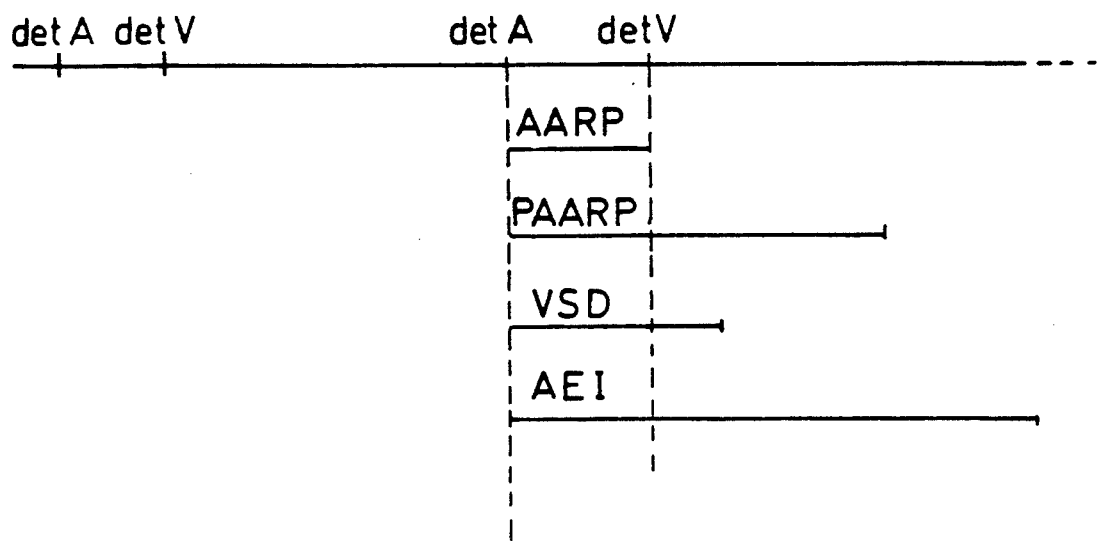
FIG. 4 is a timing diagram representing different delay periods calculated by the pacemaker in the AAI operation mode.
Figure 5:
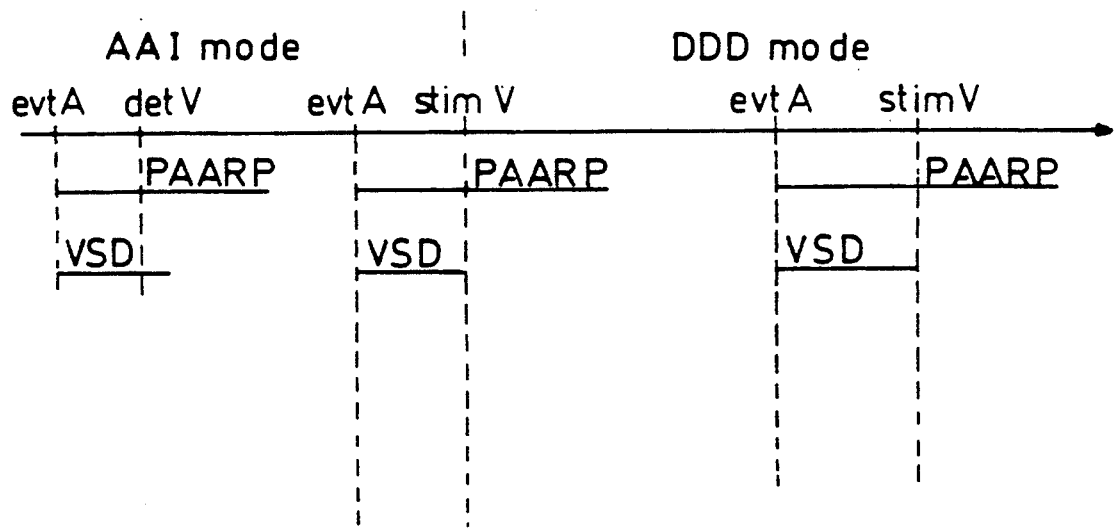
FIG. 5 is a timing diagram representing various delay periods calculated by the pacemaker upon the switching from the AAI operation mode to the DDD operation mode.

Referring to FIG. 4, in the case of the occurrence of atrial detection as long as the atrio-ventricular conduction is normal, the pacemaker operating in the AAI mode will trigger off various time delays.

One delay is the absolute atrial refractory period (AARP). This delay inhibits atrial detection until the next ventricular event. Another delay is the post-atrial atrial refractory period (PAARP). The PAARP is calculated as between 62.5 and 87.5%, and preferably 75%, of the PP interval of the preceding cardiac cycle, i.e., the time between successive atrial detections P. Any P wave occurring during the PAARP period is considered as an atrial extrasystole, which may fail to result in an atrio-ventricular conduction for reasons unrelated to whether or not there is an atrio-ventricular conduction. The occurrence of a P wave during the PAARP initiates a new atrial escape interval, i.e., the period of time when atrial pacing will occur if no spontaneous atrial depolarization is detected, but has no other influence on the pacemaker operation.

Another delay is the ventricular surveillance delay (VSD). The VSD is equivalent to the atrio-ventricular delay (AVD) of the conventional DDD mode, but is equal to the average of from 4 to 16, preferably 8, of the previous spontaneous PR intervals increased by a predetermined value of between 16 and 78 ms, preferably 47 ms, and more preferably 31 ms. The VSD period makes it possible to supervise the existence of atrio-ventricular conduction.

One other delay is atrial escape interval (AEI). The value of the AEI is calculated as a function of an average of the PP intervals over 8 cycles, using a smoothing algorithm. The smoothing algorithm provides for slowing down the sinus rate by regularly increasing the interval, for example, by a time interval in the range of 16 to 94 ms, preferably 31 ms, every 4 to 16 cycles, preferably 8 cycles, as disclosed in copending and commonly assigned U.S. application Ser. No. 07/796,003 filed Nov. 22, 1991, the disclosure of which is hereby incorporated by reference.

ATRIAL PACING

In the case of atrial pacing, as long as the atrio-ventricular conduction is normal, the pacemaker will trigger off the same delay periods as those described in connection with atrial detection, except that the delay periods may have different durations. In the atrial pacing case, the post-atrial atrial refractory period (PAARP) is set equal to 75% of the average of the 8 previous PP intervals; the ventricular surveillance delay (VSD) is set equal to the average ER interval between one atrial event and the next ventricular detection over the same selected number, preferably 8, of preceding cycles, increased by a duration comprised between 16 and 78 ms, and preferably 47 ms, more preferably 31 ms, and by the duration of the AVD extension (see FIG. 2); and the atrial escape interval AEI is equal to the value calculated with the smoothing algorithm.

As long as atrial and atrio-ventricular conductions are normal, the pacemaker will automatically calculate the values of certain parameters, namely the basic atrio-ventricular delay (basic AVD or AVDmax), the minimum atrio-ventricular delay (AVDmin), the AVD extension, and the atrial escape interval (AEI). Thus, when these parameters are being used, the operation of the device is optimized by the use of values which are adapted to the patient's most current physiology.

The algorithm for automatically adjusting the AVD as a function of the detected sinusal function uses two parameters for its operation, namely the basic AVD and the minimum AVD. In accordance with the present invention, when the rhythm is sinusal, these two parameters are automatically calculated by the pacemaker, although they are not used when the pacemaker is operating in the AAI mode. The calculated values are however, used when the pacemaker switches to operating in the DDD mode, following the appearance of a trouble in or a lack of the atrio-ventricular conduction.

Preferably, the algorithm for selecting the AVD for use in the DDD mode of pacing is a linear interpolation between the maximum and the minimum values, as a function of the sinus rhythm.

MAXIMUM AVD

In a first embodiment, when the automatic DDD mode is selected or programmed, the initial value of the AVD parameter is set to its maximum value (AVDmax), e.g., 256 ms. When the detected sinus rhythm PP is between the programmed basic pacing rate and the basic rate plus a selected percent, e.g., from 6 to 25, preferably 12.5%, the pacemaker will then calculate the average ER interval over 8 cycles. The AVDmax is again calculated so that it will tend towards this value, by fixed increments or decrements in steps of, e.g., 16 ms, such that two consecutively calculated AVDmax values may not differ by more than 16 ms. The AVDmax value is in any event maintained between its maximum value, and a minimum value, e.g., 156 ms. It should be understood that fixed step changes in AVD max and AVD min (described below) could be other than 16 ms.

In a second embodiment, when the automatic DDD mode is selected, the initial value of AVDmax is set to its minimum value, 156 ms. In this embodiment, the AVDmax also is maintained between 156 and 256 ms, and the change between two successively calculated values may not exceed the fixed step of 16 ms. The existing AVDmax value is thus compared to the average ER interval over eight cycles and when the AVDmax is shorter than the average ER interval, the value of AVDmax is increased toward the average ER interval by a maximum step of 16 ms, subject to the prescribed range.

If the average PP interval over 8 cycles is greater than or equal to the basic escape interval (corresponding to the programmed basic pacing rate) minus a first amount, e.g., between 16 and 94 ms, preferably 31 ms, and the AVDmax value is greater than or equal to the average PR interval over eight cycles plus a second amount, e.g., between 8 and 47 ms, preferably 16 ms, then the AVDmax value is reduced by a step of, e.g., 16 ms.

More preferably, the reduction of AVD is accomplished by a different technique. In this regard, if the value of AVDmax does not change during a predetermined time period, e.g., 12 to 48 hours, preferably 24 hours, then the value of AVDmax is automatically reduced by a step of 16 ms. Advantageously, this alternative provides for a simple yet elegant technique for adjusting the AVDmax value to respond to the patient's recent physiological condition more particularly, the shortening of the AVD. It also reduces memory requirements as compared to the other techniques and improves efficiency of the device.

MINIMUM AVD

The calculation of the minimum AVD parameter (AVDmin) is authorized for a detected atrial rate comprised between the programmed upper pacing rate and the upper rate less a selected percent, e.g., from 6 to 25%, preferably 12.5%, and it follows the procedure described for the maximum AVD. In other words, the AVDmin value is compared to the average ER interval over 8 cycles and when it is greater than the average ER interval, it is decreased by a step of, e.g., 16 ms. The change between successively calculated values is limited to 16 ms. Limiting the step to 16 ms limits the cycle to cycle variability of the changing and provides for relating smooth pacing changes.

When starting up the automatic DDD mode, the initial value of this parameter is set at its maximum value of, e.g., 141 ms, and it is always maintained between the maximum value and a minimum value of, e.g., 78 ms.

If the average PP interval over 8 cycles is less than or equal to the basic escape interval plus a first amount, e.g., between 16 and 94 ms, preferably 31 ms, and the AVDmin value is less than or equal to the average PR interval minus a second amount, e.g., between 8 and 47 ms, preferably 16 ms, then the AVDmin value is increased by the step of, e.g., 16 ms.

More preferably, the increase in the AVDmin value is accomplished by the simpler, different technique already discussed. In this regard, the AVDmin value is increased by a step of 16 ms if the AVDmin value has not changed during a predetermined time of from between 12 and 48, preferably 24, hours.

AVD EXTENSION

Figure 3:
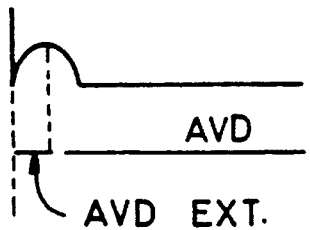
FIG. 3 is a diagram of the extension of the atrio-ventricular delay (AVD)

The AVD extension is a value which is added to the AVD after each atrial pacing. The extension makes it possible to compensate for the delay of the P wave detection in the atrium relatively to pacing (see FIG. 3). In other words, it provides a period of time from the beginning of a possible P wave to capture the height of the P wave. In the AAI mode, the nominal value of the AVD extension is typically 31 ms.

When programming the automatic DDD mode, the initial value of the AVD extension (also referred to as the AVD hysteresis) is set at a maximum value of, e.g., 125 ms. Alternatively, the nominal value of the AVD extension may be set to a maximum value of, e.g., 78 ms. In either case, the value of the AVD extension is maintained between a minimum value of, e.g., 31 ms and its maximum value.

Preferably, at each time an ER interval (paced P wave to R detection) for one cycle is shorter than the average AR for 8 cycles by more than 31 ms on one cycle, the recalculation of the AVD extension is inhibited. This is because it is assumed that there is a suspicion that a fusion phenomena, i.e., simultaneous atrial depolarization, will occur in the event of an atrial paced beat. It is calculated every time when changing from an atrial detection to an atrial pacing. The AVD extension is thus equal to the difference between, on the one hand, the interval between the atrial pacing and the next ventricular detection and, on the other hand, the PR interval measured during the last cycle. At each recalculation, the maximum change in the value is limited to a step of, e.g., 16 ms.

Upon changing from an atrial pacing to an atrial detection, the same calculation may be made but with exchanging the two intervals. The jump of one interval upon changing from atrial detection to atrial pacing, and reversely, allows to avoid a calculation error caused by overlapping of pacing and spontaneous depolarization of the atrium.

ATRIAL ESCAPE INTERVAL (AEI)

In the present invention, the smoothing algorithm associated with calculating the atrial escape interval AEI is always maintained updated based on most recent physiological activity. This occurs even though the algorithm is not used during the AAI mode of operation, so that it is available upon automatic switching to operation in the DDD mode. The atrial escape interval is therefore modified each eighth cycle, so as to be slightly longer than the average value of the PP intervals of the 8 previous cycles.

Figure 2:
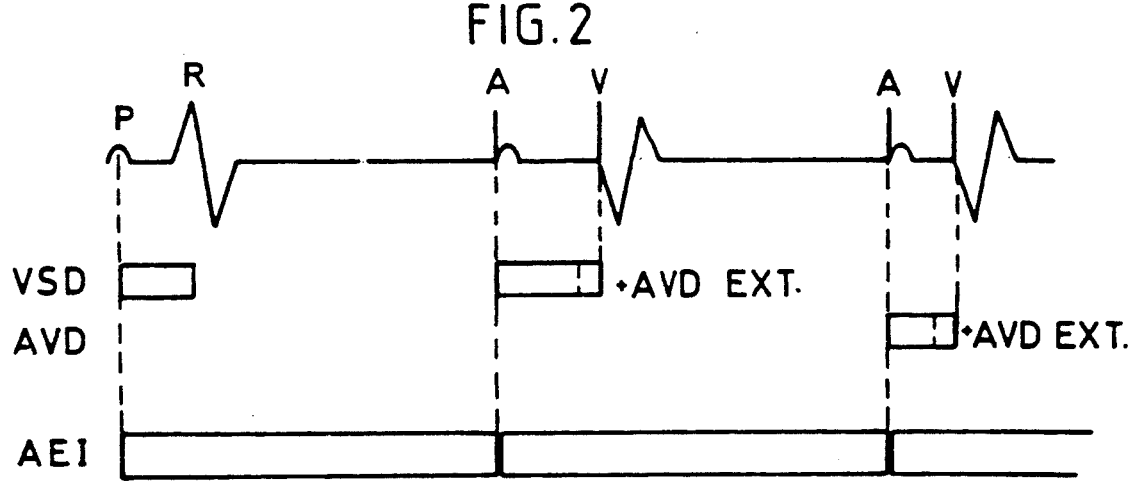
FIG. 2 is a diagram representing the cardiac signals in the case of atrial pacing, showing the switching to the DDD operation mode upon the first pacing of the ventricle.

Referring to FIG. 2, in the case of a steep slowdown of the sinusal activity, the first atrial pacing is released at the end of the atrial escape interval. Thereupon, the escape interval is lengthened by the programmed value for the deceleration slope, once for each series of 8 cycles, so as to slowly bring back the atrial pacing rate down to the basic pacing rate, if the detection of a spontaneous sinusal activity has not been detected in the meanwhile.

On another hand, through the cycles which follow the first atrial pacing, the atrial escape interval can be shortened by a programmable value defined as the acceleration slope. This has the effect of accelerating the rate of the atrial pacing, just after the sinus arrest (during 8 cycles at most), so as to attempt to compensate the inotropism drop induced by the vagal hyper-reflectivity (carotid sinus syndrome and vaso-vagal syndrome). This acceleration slope is a programmable parameter which may a zero value, in which case there is no acceleration of the pacing rate and after 8 cycles and the atrial escape interval is lengthened by the value of the deceleration slope, as described above.

If the smoothing algorithm was already being used at the moment when the automatic DDD mode is programmed, it will continue to operate as previously. Otherwise, the programming of the automatic DDD mode will initialize the programming of the smoothing algorithm, with an initial deceleration slope set at 31 ms. The acceleration slope is an independent parameter which may be voluntarily programmed and has a default or initial value of zero. Preferably, the deceleration slope is selected from the range of 16 to 94 ms and the acceleration slope is selected from the range of 16 to 188 ms as described in the U.S. Ser. No. 07/796,003.

Figure 1:
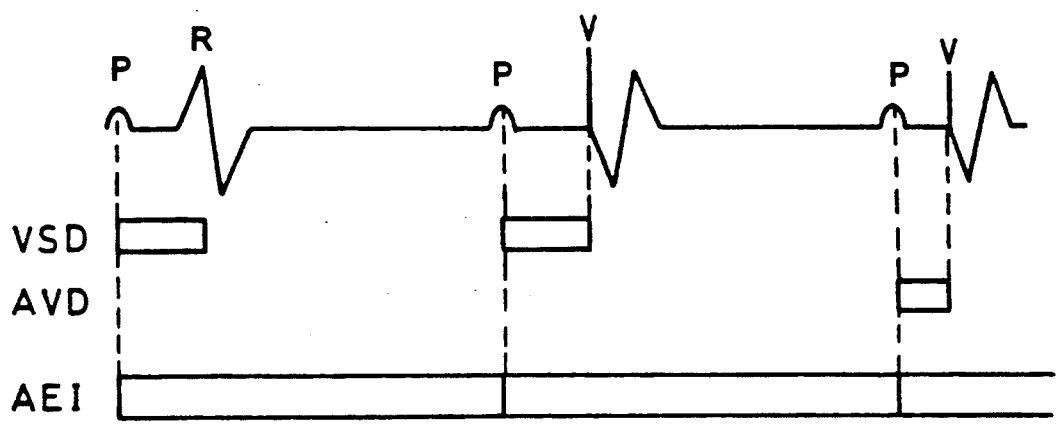
FIG. 1 is a diagram representing the cardiac signals in the case of atrial detection, showing the switching to the DDD operation mode upon the first pacing of the ventricle.

Referring to FIG. 1, the left hand side illustrates the physiological signals of a heart controlled by the pacemaker operating in the AAI mode. A spontaneous ventricular depolarization R occurs before the end of the ventricle surveillance delay (VSD). In the middle of FIG. 1, the physiological heart signals illustrate that the ventricle is paced, as indicated by the reference character V, at the end of the VSD. This pacing corresponds to the switching over of the pacemaker to the DDD mode, which continues through the right hand side of FIG. 1.

Referring to FIG. 2, the physiological signals in the left hand portion correspond to the physiological functions of the heart controlled by a pacemaker operating in the AAI mode. In the middle of FIG. 2, the atrium is paced, as indicated by the reference character A, at the end of the atrial escape interval, by the pacemaker which is still operating in the AAI mode. As a result of the pacing of the atrium, the ventricular surveillance delay is lengthened by the value of the AVD extension, which always corresponds to the AAI mode.

When, at the end of the lengthened VSD, the pacemaker ascertains the absence of a ventricular detection, it paces the ventricle and automatically switches to the DDD operating mode, as illustrated in the right hand portion of FIG. 2.

Thus, in the absence of a ventricular detection R before the end the ventricular surveillance delay (VSD), the pacemaker switches over to the DDD operation mode, using the previously calculated values for the AVDmin, AVDmax, the AVD extension and the AEI. In this way, the switching over to the DDD mode takes place with optimized parameters which correspond to the patient's condition at the moment of switching over.

The process of the reversal of the pacemaker to the AAI mode takes place as soon as one of the following conditions is met:

(1) recovery of a spontaneous ventricular activity (a ventricular detection R occurs before the end of the AVD), (2) transition from a paced atrial activity A to an atrial detection P (which may be indicating the end of a vagal syndrome), (3) after 100 cycles with ventricular pacing (because the automatic DDD mode is intended for use with paroxystic conduction troubles), or (4) when the frequency of events, i.e., either the spontaneous detection A or pacing P rate, becomes less than or equal to a reference frequency selected to correspond to the basic pacing rate.

As soon as one of the above conditions is met, the calculated value for the AVD is systematically increased by a duration comprised between 16 and 78 ms, and preferably equal to 47 ms, more preferably equal to 31 ms, for enhancing the recovery of the ventricular detection.

If, during the extended AVD, the pacemaker does not record any ventricular detection R, it will then pace the ventricle at the end of this delay.

Regarding the fourth condition for the reversion from the DDD mode to the AAI mode, the reference frequency is predetermined and corresponds to a ventricular escape interval and preferably is equal to a basic escape interval less a selected delay period, which is preferably 31 ms. As soon as this condition is satisfied, the calculated value for the AVD is increased by the selected delay period. If the spontaneous ventricular activity R does not resume, the extension of 31 ms is suppressed as soon as the sinus frequency becomes greater than the predetermined reference frequency.

Preferably, the recovery of spontaneous ventricular activity occurs when, during 16 consecutive cycles, the pacemaker detects ventricular depolarization R events which are synchronous with atrial events. It will then automatically revert to the AAI operation mode.

The method of the invention is preferably performed by a computer, more preferably, a microprocessor device having software instructions in an associated memory device and sensors suitable for performing the measurements described and providing stimulating pulses as appropriate, including without limitation, a microprocessor controlled dual chamber pacemaker having input parameters programmable for the patient's characteristics in the known manner. Appropriate devices for converting analog circuit signals to digital signals and vice versa may be provided. It is to be understood, however, that the method also may be performed by suitable analog circuit devices, and by a combination of digital and analog circuits. All of the foregoing components are conventional.

Figure 6:
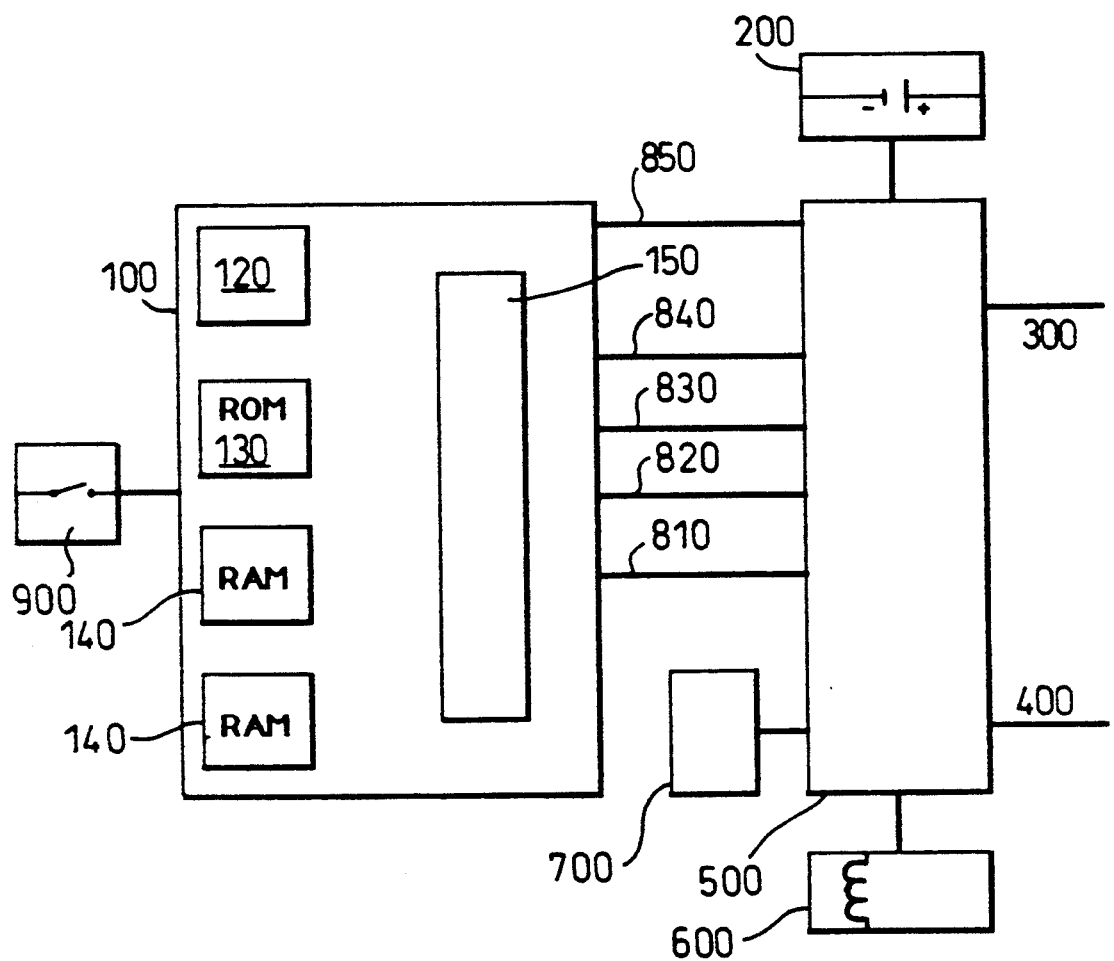
FIG. 6 is a schematic block diagram of an embodiment of a pacemaker incorporating the present invention.

Referring to FIG. 6, a schematic embodiment of a dual chambered pacemaker capable of operating in a DDD pacing mode in accordance with the present invention is illustrated. The apparatus includes a microprocessor 100, a battery 200, an atrial sensing and pacing catheter 300, a ventricular sensing and pacing catheter 400, an analog signal acquisition and conversion circuit 500, a telemetry antenna 600, and an associated reed switch 900, a clock oscillator 700 and appropriate data and control buses.

Microprocessor 100 is preferably an eight bit device including a central processing unit 120, a ROM-type memory device 130 which includes software instructions for operating the pacemaker including inter alia in accordance with the present invention, one or more RAM-type memory devices 140 for data storage, manipulation and other memory related functions, and an input/output interface 150 for communicating within microprocessor 100 and between microprocessor 100 and other components of the pacemaker. Input/output interface 150 includes, for example, a data bus 810 for data transmission, an address bus 820, a control bus 830, all of which are conventional and dependent on the microprocessor device used.

Catheters 300 and 400 are conventional pacemaker catheter electrodes and preferably have associated conventional protection circuits (not shown) to protect the pacemaker and patient from external signals in the usual manner and a conventional pacing pulse generator (not shown).

Circuit 500 provides for converting analog cardiac atrial and ventricular signals to digital signals (and for converting digital signals to analog signals) for signal processing by microprocessor 100, and does not itself form any part of the present invention.

Antenna 600 is used for remote programming of microprocessor 100 in cooperation with actuation reed switch 900, in the conventional manner. Antenna 600 also may be provided with suitable protection circuits. Oscillator 700 provides the base clock frequency for operating the data acquisition and processing functions. The foregoing components are available in one form or another and may be assembled by a person of ordinary skill in the art.

A preferred microprocessor controlled dual chamber pacemaker for use with the present invention is an atrial based pacemaker such as the model CHORUS TM or CHORUS II TM, implantable dual chamber pulse generator DDD MO, available from Ela Medical, Montrouge, France. The model CHORUS II 6200 Series, specifically the 6234, includes an operating mode that uses the present invention when the "automatic DDD" mode is programmed on.

A preferred embodiment of a software program useful for controlling a microprocessor controlled dual-chambered pacemaker in accordance with the present invention is set forth in the microfiche appendix. Preparation of alternate suitable software for controlling such microprocessor controlled pacemakers, and for reprogramming known microprocessor controlled dual chamber pacemakers, to operate in accordance with the present invention is believed to be well within the ability of a person of ordinary skill in the art.

Advantageously, the present invention preserves spontaneous ventricular contraction in order to optimize myocardial function. It also allows the following objectives to be met: sustained spontaneous AV conduction preserving physiological synchronization of ventricular contraction-relaxation, conservation of pacemaker energy, minimization of the effects of intermittent AV block, and ensuring continuous preservation of AV synchrony. The present invention allows for minimizing ventricular pacing followed by retrograde conduction after a ventricular extrasystole and loss of AV synchrony during intermittent AV block in DDI mode, and reducing risk of endless loop tachycardia by reducing the extent of pacing in classic DDD mode.

One skilled in the art will appreciate that the present invention can be practiced by other than the described embodiments which are presented for purposes of illustration and not of limitation.

We claim:

1. In a cardiac pacemaker having a AAI mode of operation and a DDD mode of operation, a method of switching between modes of operation comprising:

monitoring atrial events including atrial detection and atrial pacing outside of a selected refractory period;

selecting a ventricular surveillance delay period following the occurrence of a sensed atrial event;

monitoring atrio-ventricular conduction following each sensed atrial event during the selected ventricular surveillance delay period; and operating the pacemaker in the DDD mode of operation if there is no sensed atrio-ventricular conduction during the ventricular surveillance delay period and operating the pacemaker in the AAI mode of operation if there is atrio-ventricular conduction during the ventricular surveillance delay period.

2. The method of claim 1 wherein selecting the ventricular surveillance delay further comprises averaging a first interval between one atrial event and the subsequent ventricular detection during a first plurality of cycles and increasing the averaged first interval by a first predetermined duration.

3. The method of claim 2 wherein the first plurality is selected from between 4 and 16 and the first predetermined duration is selected from between 16 and 78 ms.

4. The method of claim 3 further comprising limiting the maximum duration of the ventricular surveillance delay to 350 ms.

5. The method of claim 1 further comprising, at the time of switching to operating in the DDD mode, calculating an atrio-ventricular delay using linear interpolation between a preselected maximum delay value and a preselected minimum delay value as a function of the rhythm of atrial events.

6. The method of claim 5 further comprising preselecting the maximum and minimum delay values as the maximum and minimum values respectively of the atrio-ventricular delay sensed during the period of spontaneous atrio-ventricular conduction prior to switching to operating in the DDD mode.

7. The method of claim 6 wherein the pacemaker is provided with a minimum pacing rate and wherein preselecting the maximum delay value further comprises selecting the maximum value of the atrio-ventricular delay when the atrial event rhythm is between the minimum pacing rate and the minimum pacing rate increased by a percent selected from between 6% and 25%.

8. The method of claim 6 wherein the pacemaker is provided with a maximum pacing rate and wherein preselecting the minimum delay value further comprises selecting the minimum value of the atrio-ventricular delay when the atrial event rhythm is between the maximum pacing rate and the maximum pacing rate lessened by a percent selected from between 6% and 25%.

9. The method of claim 6 wherein preselecting the maximum delay value further comprises:

determining an average of the interval between one atrial event and the subsequent ventricular detection over a plurality of cycles for each plurality of cycles, the plurality of cycles being selected from between 4 and 16 cycles;

comparing the maximum delay to each determined average interval; and increasing the maximum delay value by a first time interval selected from between 8 and 47 ms each time the compared maximum delay value is less than one said average interval, provided that the maximum delay value is maintained between selected maximum and minimum values.

10. The method of claim 6 wherein preselecting the maximum delay further comprises reducing the maximum delay value by a second time interval selected from between 8 and 94 ms if the maximum delay value is not changed during a time period selected in the range of from 12 to 48 hours.

11. The method of claim 6 wherein the pacemaker is provided with a minimum pacing rate having a basic escape interval, and wherein preselecting the maximum delay further comprises:

calculating a first average of the interval between successive atrial events over a first number of cycles, the first number being selected from between 4 and 16;

calculating a second average of the interval between each atrial event and the following ventricular detection over the same first number of cycles; and reducing the maximum delay by a first amount selected from between 8 and 94 ms if the maximum delay over one cycle is greater than the second average plus a second amount and the first average is greater than the basic escape interval minus a third amount, the second amount being selected from between 8 and 47 ms, the third amount being selected from between 16 and 94 ms.

12. The method of claim 6 wherein the pacemaker is provided with a maximum pacing rate having a minimum escape interval, and wherein preselecting the minimum delay further comprises:

calculating a first average of the interval between successive atrial events over a first number of cycles, the first number being selected from between 4 and 16;

calculating a second average of the interval between each atrial event and the following ventricular detection over the same first number of cycles; and increasing the minimum delay by a first amount selected from between 8 and 94 ms if the minimum delay over one cycle is less than or equal to the second average minus a second amount and the first average is less than or equal to the minimum escape interval plus a third amount, the second amount being selected from between 8 and 47 ms, the third amount being selected from between 16 and 94 ms.

13. The method of claim 6 wherein preselecting the minimum delay value further comprises:

determining an average of the interval between one atrial event and the subsequent ventricular detection over a plurality of cycles for each plurality of cycles, the plurality of cycles being selected from between 4 and 16 cycles;

comparing the minimum delay to each determined average interval; and decreasing the minimum delay value by a first time interval selected from between 8 and 47 ms each time the compared minimum delay value is greater than one said average interval, provided that the minimum delay value is maintained between selected maximum and minimum values.

14. The method of claim 6 wherein preselecting the minimum delay further comprises increasing the minimum delay by a second time interval selected from between 8 and 94 ms if the minimum delay is not changed during a time period selected in the range of from 12 to 48 hours.

15. The method of claim 1 further comprising:
determining a switch from atrial detection to atrial pacing;
calculating an extension of the atrio-ventricular delay as the difference between a first interval and a second interval, the first interval being the period between the atrial pacing and the following ventricular detection, and the second interval being the difference between the atrial detection and the next ventricular detection, the second interval being measured during the antepenultimate cycle.

16. The method of claim 1 further comprising:
determining a switch from atrial pacing to atrial detection;
calculating an extension of the atrio-ventricular delay as the difference between a first interval and a second interval, the first interval being the period between the atrial pacing and the next ventricular detection, and the second interval being the difference between the atrial detection and the following ventricular detection, the first interval being measured during the antepenultimate cycle.

17. The method of claim 1 wherein operating in the DDD mode further comprises switching to operation to the AAI mode in response to the occurrence of one of a change from a paced atrial event to an atrial detection, recovery of spontaneous ventricular activity over a first selected number of cycles, the occurrence of a second selected number of cycles with ventricular pacing, and when the spontaneous detection or pacing rate becomes less than a selected reference frequency corresponding to the basic escape interval less a selected time period.

18. The method of claim 17 wherein the first selected number is on the order of 16 cycles and the second selected number is on the order of 100 cycles.

19. The method of claim 1 wherein the pacemaker is provided with a minimum pacing rate having a basic escape interval, further comprising:
selecting a reference rate corresponding to the basic escape interval minus a first delay;
comparing the rate of atrial events to the predetermined reference rate; and
prolonging the atrio-ventricular delay by a selected amount in the range of from 16 to 78 ms if the atrial event rate is less than or equal to the reference rate.

20. The method of claim 1 further comprising:
determining a switch from atrial detection to atrial pacing;
shortening the atrial escape interval by a first amount over a first plurality of cycles in response to a switch, the first plurality being selected from between 4 and 16, the first amount being selected from between 16 and 188 ms.

21. A cardiac pulse generator having an AAI mode of operation for sensing atrial events including spontaneous and paced depolarizations and for providing atrial pacing pulses and a DDD mode of operation for providing ventricular pacing pulses in response to an atrial event comprising:

a circuit for monitoring atrio-ventricular conduction in response to an atrial event;
a switch having a first condition for operating the pulse generator in the AAI mode and a second condition for operating the pulse generator in the DDD mode;
a first means for changing the switch from the first condition to the second condition in response to the absence of a synchronous atrio-ventricular conduction following an atrial event; and
a second means for changing the switch from the second condition to the first condition in response to a restoration event.

22. The apparatus of claim 21 wherein the circuit further comprises:
means for calculating an average of a first interval between one atrial event and the subsequent ventricular detection during a first plurality of cycles; and
means for providing a ventricular surveillance delay corresponding to the average value of said first interval increased by a first predetermined duration, such that the circuit monitors atrio-ventricular conduction following an atrial event during the ventricular surveillance delay.

23. The apparatus of claim 22 wherein the first plurality is selected from between 4 to 16 and the first predetermined duration is selected from between 16 and 78 ms.

24. The apparatus of claim 23 wherein the ventricular delay has a maximum duration of 350 ms.

25. The apparatus of claim 21, further comprising a means for calculating an atrio-ventricular delay for use in the DDD mode using linear interpolation between a preselected maximum delay value and a preselected minimum delay value as a function of the rhythm of atrial events.

26. The apparatus of claim 25 wherein the maximum and minimum delay values are the calculated maximum and minimum values respectively of the atrio-ventricular delay sensed during the period of spontaneous atrio-ventricular conduction prior to switching to operating in the DDD mode.

27. The apparatus of claim 26 wherein the pacemaker is provided with a minimum pacing rate and the maximum delay value is the sensed maximum value of the atrio-ventricular delay when the atrial event rhythm is between the minimum pacing rate and the minimum pacing rate increased by a percent selected from between 6% and 25%.

28. The apparatus of claim 26 wherein the pacemaker is provided with a maximum pacing rate and the minimum delay value is the sensed minimum value of the atrio-ventricular delay when the atrial event rhythm is between the maximum pacing rate and the maximum pacing rate lessened by a percent selected from between 6% and 25%.

29. The apparatus of claim 26 further comprising:
means for determining an average of the interval between one atrial event and the subsequent ventricular detection over a plurality of cycles for each plurality of cycles, the plurality of cycles being selected from between 4 and 16 cycles;
means for comparing the maximum delay to each determined average of the first interval; and
means for increasing the maximum delay value by a first time interval selected from between 8 and 94 ms each time the compared maximum delay value is less than one said first average, provided that the maximum delay value is maintained between selected maximum and minimum values.

30. The apparatus of claim 26 further comprising means for reducing the maximum delay by a time interval selected from between 8 and 94 ms if the maximum delay value is not changed during a time period selected in the range of from 12 to 48 hours.

31. The apparatus of claim 26 wherein the pacemaker is provided with a minimum pacing rate having a basic escape interval, further comprising:
   means for calculating a first average of the interval between successive atrial events over a first number of cycles, the first number being selected from between 4 and 16;
   means for calculating a second average of the interval between each atrial event and the following ventricular detection over the same first number of cycles; and
   means for reducing the maximum delay by a first amount selected from between 8 and 94 ms if the maximum delay is greater than the second average plus a second amount and the first average is greater than the basic escape interval minus a third amount, the second amount being selected from between 8 and 47 ms, the third amount being selected from between 16 and 94 ms.

32. The apparatus of claim 26 wherein the pacemaker is provided with a maximum pacing rate having a minimum escape interval, further comprising:
   means for calculating a first average of the interval between successive atrial events over a first number of cycles, the first number being selected from between 4 and 16;
   means for calculating a second average of the interval between each atrial event and the following ventricular detection over the same first number of cycles; and
   means for increasing the minimum delay by a first amount selected from between 8 and 94 ms if the minimum delay over one cycle is less than or equal to the second average minus a second amount and the first average is less than or equal to than the minimum escape interval plus a third amount, the second amount being selected from between 8 and 47 ms, the second amount being selected from between 16 and 94 ms.

33. The apparatus of claim 26 further comprising:
   means for determining an average of the interval between one atrial event and the subsequent ventricular detection over a plurality of cycles for each plurality of cycles, the plurality of cycles being selected from between 4 and 16 cycles;
   means for comparing the minimum delay to each determined average of the interval; and
   means for decreasing the minimum delay value by a first time interval selected from between 8 and 47 ms each time the compared minimum delay value is greater than one said average interval, provided that the minimum delay value is maintained between selected maximum values.

34. The apparatus of claim 26 further comprising means for increasing the minimum delay by a time interval selected from between 8 and 94 ms if the minimum delay is not changed during a selected time period in the range of from 12 to 48 hours.

35. The apparatus of claim 2 further comprising means for calculating an extension of the atrio-ventricular delay as the difference between a first interval and a second interval, the first interval being the period between the atrial pacing and the following ventricular detection, and the second interval being the difference between the atrial detection and the next ventricular detection, the second interval being measured during the antepenultimate cycle prior to a switch from atrial detection to atrial pacing.

36. The apparatus of claim 21 further comprising means for calculating an extension of the atrio-ventricular delay as the difference between a first interval and a second interval, the first interval being the period between the atrial pacing and the next ventricular detection, and the second interval being the difference between the atrial detection and the following ventricular detection, the first interval being measured during the antepenultimate cycle prior to a switch from atrial pacing to atrial detection.

37. The apparatus of claim 21 wherein the restoration event is selected from among the group consisting of a detected atrio-ventricular conduction occurring synchronous with an atrial event over a first selected number of cycles, a detected spontaneous atrial depolarization following a preceding atrial pacing pulse, the occurrence of a second selected number of cycles with ventricular pacing, and when the spontaneous detection or pacing rate becomes less than a selected reference frequency corresponding to the basic escape interval less selected delay period.

38. The apparatus of claim 37 wherein the first selected number is on the order of 16 cycles and the second selected number is on the order of 100 cycles.

39. The apparatus of claim 21 wherein the pacemaker is provided with a minimum pacing rate having a basic escape interval, and a reference rate corresponding to the basic escape interval minus a first delay, further comprising means for comparing the rate of atrial events to the predetermined reference rate and prolonging the atrio-ventricular delay by a selected amount in the range of from 16 to 78 ms if the atrial event rate is less than or equal to the reference rate.

40. The apparatus of claim 21 further comprising means for shortening the atrial escape interval by a first amount over a first plurality of cycles in response to a switch from atrial detection to atrial pacing, the first plurality being selected from between 4 and 16, the first amount being selected from between 18 and 188 ms.

* * * * *

UNITED STATES PATENT AND TRADEMARK OFFICE
CERTIFICATE OF CORRECTION

PATENT NO. : 5,318,594
DATED : June 7, 1994
INVENTOR(S) : Limousin et al.

It is certified that error appears in the above-indentified patent and that said Letters Patent is hereby corrected as shown below:

Title Page, "[*] Notice. . . subsequent to has been disclaimed" and the asterisk at the patent issue date should be deleted;

Column 1, line 35, after "appropriate insert --.--.

Column 16, line 9, "2" should be --21--.

Signed and Sealed this

Twenty-ninth Day of November, 1994

Attest:

BRUCE LEHMAN

Attesting Officer

Commissioner of Patents and Trademarks